(12) United States Patent
Kim et al.

(10) Patent No.: US 12,424,324 B2
(45) Date of Patent: Sep. 23, 2025

(54) META INFORMATION EXTRACTION DEVICE OF OBJECT FOR ARTIFICIAL INTELLIGENCE ART PSYCHOLOGICAL TEST AND ART PSYCHOLOGICAL ANALYSIS SYSTEM AND METHOD USING THE SAME

(71) Applicant: I-SCREAM ARTS CO., LTD., Seoul (KR)

(72) Inventors: Ji-hoon Kim, Seoul (KR); Ki-seok Park, Seoul (KR)

(73) Assignee: I-SCREAM ARTS CO., LTD., Seoul (KR)

(*) Notice: Subject to any disclaimer, the term of this patent is extended or adjusted under 35 U.S.C. 154(b) by 293 days.

(21) Appl. No.: 18/350,919

(22) Filed: Jul. 12, 2023

(65) Prior Publication Data

US 2023/0352177 A1  Nov. 2, 2023

Related U.S. Application Data

(63) Continuation of application No. PCT/KR2021/016755, filed on Nov. 16, 2021.

(30) Foreign Application Priority Data

Sep. 3, 2021 (KR) .................. 10-2021-0117708
Nov. 11, 2021 (KR) .................. 10-2021-0154399

(51) Int. Cl.
*G16H 50/20* (2018.01)

(52) U.S. Cl.
CPC .................... *G16H 50/20* (2018.01)

(58) Field of Classification Search
CPC ........ G16H 50/20; G16H 10/20; G16H 50/70; A61B 5/00; A61B 5/16; G06V 10/24
See application file for complete search history.

(56) References Cited

U.S. PATENT DOCUMENTS

| | | | | |
|---|---|---|---|---|
| 10,402,061 | B2* | 9/2019 | Kohlmeier | G06F 3/0482 |
| 2012/0116186 | A1* | 5/2012 | Shrivastav | G10L 25/48 |
| | | | | 600/301 |
| 2023/0081601 | A1* | 3/2023 | Wang | A61B 6/488 |
| | | | | 378/96 |

FOREIGN PATENT DOCUMENTS

| | | | |
|---|---|---|---|
| KR | 10-2011-0092949 A | 8/2011 | |
| KR | 10-1524753 B1 | 6/2015 | |

(Continued)

OTHER PUBLICATIONS

Stachl et al. "Personality Research and Assessment in the Era of Machine Learning." European Journal of Personality. vol. 34, Issue 5. First published online Sep. 1, 2020. (Year: 2020).*

(Continued)

*Primary Examiner* — Linh Giang Le
(74) *Attorney, Agent, or Firm* — NKL Law; Jae Youn Kim (57) ABSTRACT

Provided is a meta information extraction device of an object for artificial intelligence art psychological test and an art psychological analysis system and method using the same. The meta information extraction device extracts an object and meta information of the object from picture data by means of training of an artificial intelligence model, and analyzes picture data of a user who is a test taker with a combination of meta information to analyze a psychological state of the user. A meta information extraction device of an object for an artificial intelligence art psychological test according to the present disclosure may include, a user interface for providing an interactive environment to a user who is a test taker, a first feature extraction unit which is trained by an artificial intelligence model to extract the object from picture data generated on a screen using an object selected by the user through the user interface, a second feature extraction unit which is trained by an artifi- (Continued)

cial intelligence model to extract meta information of an object extracted by the first feature extraction unit, and a library which stores the object extracted by the first feature extraction unit and the meta information extracted by the second feature extraction unit.

12 Claims, 4 Drawing Sheets

(56) References Cited

FOREIGN PATENT DOCUMENTS

| | | |
|---|---|---|
| KR | 10-1898385 B1 | 9/2018 |
| KR | 10-1926836 B1 | 12/2018 |
| KR | 10-1942444 B1 | 1/2019 |
| KR | 102240930 B1 * | 4/2021 ........... A61B 5/7275 |

OTHER PUBLICATIONS

Kim, S.-K. et al. Development of fuzzy reasoning based psychological diagnosis application with automatic hand-drawing analysis. Journal of Digital Contents Society. Mar. 2021, vol. 22, No. 3, pp. 519-525. See pp. 521-524, and figures 1-2.

Jeon, In-Ho et al., Computerized Psychological Test System for Art Therapy. Journal of KIISE : Computing Practices and Letters. 2010, vol. 16, No. 2, pp. 135-143 See pp. 137-138.

* cited by examiner

META INFORMATION EXTRACTION DEVICE OF OBJECT FOR ARTIFICIAL INTELLIGENCE ART PSYCHOLOGICAL TEST AND ART PSYCHOLOGICAL ANALYSIS SYSTEM AND METHOD USING THE SAME

TECHNICAL FIELD

The present disclosure relates to a meta information extraction device of an object for an artificial intelligence art psychological test and art psychological analysis system and method using the same, and more particularly, to a technique of extracting an object and meta information of the object from picture data by training an artificial intelligence model, and analyzing picture data of a user who is a test taker with a combination of meta information to analyze a psychological state of the user.

BACKGROUND ART

Artificial intelligence learning such as deep learning requires high quality and large volume of training data. Even though some data is open for research, due to lack or insufficiency of the data, the artificial intelligence learning cannot be frequently applied.

Training data for training the artificial intelligence model is labeled to be learned by the artificial intelligence model after collecting the data. In order to apply the artificial intelligence model to a field of art psychological analysis using picture data including objects, there are massive types and expressions of pictures to be learned by the artificial intelligence model, like subjective problems so that there are problems in that it takes a lot of time and cost to collect the training data, and the artificial intelligence learning may not be accurately performed.

Accordingly, in order to construct the artificial intelligence model in the field of art psychological analysis, it is necessary to train the artificial intelligence model by collecting cleansed training data which limits a dimension and a range, like multiple-choice questions.

DISCLOSURE

Technical Problem

An object of the present disclosure is to provide a meta information extraction device of an object for an artificial intelligence art psychological test, the device which enables to construct and train an artificial intelligence model for art psychological analysis by extracting an object and meta information of the object from picture data to limit a dimension and a range.

Further, an object of the present disclosure is to provide an art psychological analysis system and method which analyze a psychological state of a user who is a test taker by a combination of meta information of an object in which a psychological analysis opinion of a tester is added.

Further, an object of the present disclosure is to provide an art psychological analysis system and method which also help a test taker who lacks a drawing skill to express a subject to take the art psychological test by generating picture data by selecting objects stored in a library.

Technical objects to be achieved in the present disclosure are not limited to the aforementioned technical objects, and another not-mentioned technical object will be clearly understood by those skilled in the art from the description below.

Technical Solution

In order to achieve the above-described objects, a meta information extraction device of an object for an artificial intelligence art psychological test according to the present disclosure may include a user interface for providing an interactive environment to a user who is a test taker; a first feature extraction unit which is trained by an artificial intelligence model to extract the object from picture data generated on a screen using an object selected by the user through the user interface; a second feature extraction unit which is trained by an artificial intelligence model to extract meta information of the object extracted by the first feature extraction unit; and a library which stores the object extracted by the first feature extraction unit and the meta information extracted by the second feature extraction unit.

Further, the picture data may be configured by a combination of objects generated in a position designated by the user after being selected from the library through the user interface by the user.

The first feature extraction unit may extract detailed picture information with an area set in the picture data as a background, and extract an object from the detailed picture information.

Further, the first feature extraction unit transforms or adjusts a size value, an angle value, and a position value of an object extracted from the detailed picture information to a size value, an angle value, and a position value which are applicable to the picture data to extract a plurality of objects from one object.

Further, the second feature extraction unit may extract each meta information of the object including at least a type, a size value, an angle value, and a position value of the object from the plurality of objects.

The position value of the object may be a coordinate of a center pixel, among pixels which configure the object generated by preprocessing detailed picture information including an object from which the meta information is to be extracted by the second feature extraction unit in pixel units.

A size value of the object may include, based on the object extracted from the detailed picture information, a magnification of reducing or enlarging the object from which the meta information is to be extracted, and width and length values of the object.

The width and length values of the object may be calculated by x and y coordinate values of each pixel which forms sets of outer pixels enclosing the object, among pixels which configure the object which is generated by preprocessing the detailed picture information including an object from which the meta information is to be extracted by the second feature extraction unit, in the pixel units.

The angle value of the object may be a rotating degree of an object from which the meta information is to be extracted, based on an angle value of an object extracted from the detailed picture information.

An art psychological analysis system using a meta information extraction device of an object for an artificial intelligence art psychological test according to the present disclosure may include a meta information extraction device which is trained by an artificial intelligence model to extract the object from picture data generated on a screen by selecting an object by a user who is a test taker and meta information from the object and stores the extracted object and meta information; a meta information preprocessing device which receives the meta information from the meta information extraction device and a psychological analysis opinion obtained by analyzing the meta information input from a terminal of a second user who is a tester, and adds the psychological analysis opinion to the meta information; and a psychological state analysis device which is trained by an artificial intelligence model to analyze a psychological state of the user with a combination of meta information to which a psychological analysis opinion received from the meta information preprocessing device is added.

Further, the meta information extraction device receives information about a psychological state of the user from the psychological state analysis device, and may display information about a psychological state of the user on a screen of the meta information extraction device after removing the picture data.

An art psychological analysis method using a meta information extraction device of an object for an artificial intelligence art psychological test according to the present disclosure may include training a meta information extraction device and a psychological state analysis device; generating picture data on a screen of the meta information extraction device using an object selected by a user who is a test taker through a user interface; storing the object and meta information, by the meta information extraction device, after extracting the object from the picture data and the meta information from the object; transmitting the meta information, by a meta information preprocessing device, to a terminal of a second user who is a tester, after receiving the meta information from the meta information extraction device; allowing the second user to input a psychological analysis opinion obtained by analyzing meta information through a terminal of the second user and transmit the psychological analysis opinion to the meta information preprocessing device; adding the psychological analysis opinion received from the terminal of the second user to meta information, by the meta information preprocessing device; and analyzing a psychological state of the user with a combination of meta information to which the psychological analysis opinion received from the meta information preprocessing device, by the psychological state analysis device.

Further, the art psychological analysis method using a meta information extraction device of an object for an artificial intelligence art psychological test according to the present disclosure may further include receiving information about a psychological state of the user, by the meta information extraction device, from the psychological state analysis device, and displaying information about a psychological state of the user on a screen of the meta information extraction device after removing the picture data.

A computer program stored in a computer readable recording medium to execute an art psychological analysis method using a meta information extraction device of an object for an artificial intelligence art psychological test of the present disclosure may be provided.

Advantageous Effects

According to the present disclosure, a dimension and a range of a problem to be trained by the artificial intelligence model are limited by extracting meta information about the object to easily construct and train an artificial intelligence model for art psychological analysis.

Further, according to the present disclosure, a psychological state of a user who is a test taker may be analyzed with a combination of meta information in which a psychological analysis opinion of a tester is added to the meta information extracted from the object.

According to the present disclosure, the test taker may be provided with the psychological analysis only by selecting objects stored in a library to generate the picture data, rather than directly drawing the picture data so that a time required for the psychological analysis is saved.

Further, according to the present disclosure, the picture data is formed by selecting objects stored in a library so that it is possible to help a test taker who lacks drawing skills to express the subject to be provided with the art psychological test.

A technical object to be achieved in the present disclosure is not limited to the aforementioned effects, and other not-mentioned effects will be obviously understood by those skilled in the art from the description below.

BEST MODE

Hereinafter, exemplary embodiments of the present disclosure will be described more fully with reference to the accompanying drawings for those skilled in the art to easily implement the present disclosure. Description of the present disclosure is just an embodiment for structural and functional description so that the scope of the present disclosure is not interpreted to be limited by the embodiment described in the specification. That is, the embodiment may be modified in various forms so that it is understood that the scope of the present disclosure has equivalents which are capable of implementing the technical spirit. Further, it does not mean that the specific embodiment includes the object or effect proposed in the present disclosure or includes only the effect so that it is not understood that the scope of the present disclosure is limited thereby.

In the meantime, meanings of terms described in the present disclosure can be understood as follows.

The terms "first" or "second" are used to distinguish one component from the other component so that the scope should not be limited by these terms. For example, a first component may be referred to as a second component, and similarly, a second component may be referred to as a first component. It should be understood that, when it is described that an element is "connected" to another element, the element may be directly connected to the other element or connected to the other element through a third element. In contrast, it should be understood that, when it is described that an element is directly connected to another element, no element is present between the element and the other element. Other expressions which describe the relationship between components, that is, "between" and "directly between", or "adjacent to" and "directly adjacent to" need to be interpreted by the same manner.

Unless the context apparently indicates otherwise, it should be understood that terms "include" or "have" indicate that a feature, a number, a step, an operation, a component, a part or the combination thereof described in the specification is present, but do not exclude a possibility of presence or addition of one or more other features, numbers, steps, operations, components, parts or combinations thereof, in advance.

Unless they are contrarily defined, all terms used herein including technological or scientific terms have the same meaning as those generally understood by a person with ordinary skill in the art. Terms which are defined in a generally used dictionary should be interpreted to have the same meaning as the meaning in the context of the related art but are not interpreted as an ideally or excessively formal meaning if it is not clearly defined in the present disclosure.

A meta information extraction device 10 of an object for an artificial intelligence art psychological test according to the present disclosure (hereinafter, referred to as "meta information extraction device 10") is a device which extracts an object and meta information 130 of the object from picture data 100 to train an artificial intelligence model for art psychological analysis, and components of the device for implementing this are as follows.

Figure 1:
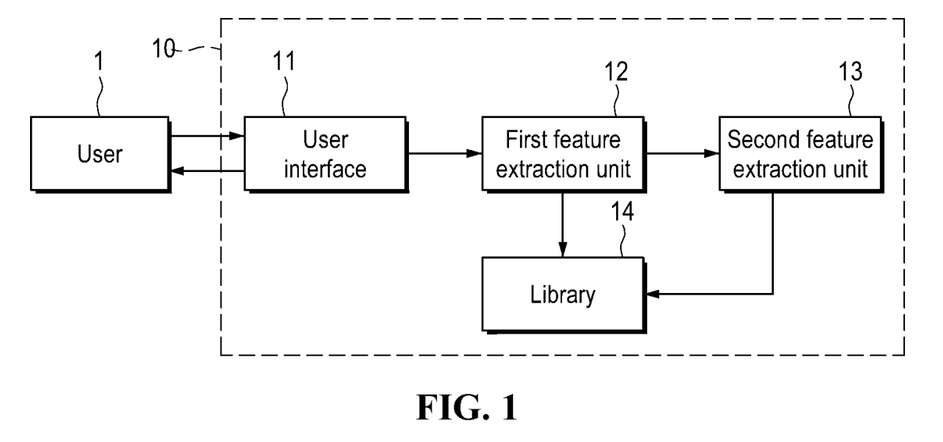
FIG. 1 is a block diagram schematically illustrating a meta information extraction device of an object for an artificial intelligence art psychological test according to the present disclosure.

FIG. 1 is a block diagram schematically illustrating a meta information extraction device of an object for an artificial intelligence art psychological test according to the present disclosure.

Referring to FIG. 1, a meta information extraction device 10 according to the present disclosure includes a user interface 11, a first feature extraction unit 12, a second feature extraction unit 13, and a library 14.

The user interface 11 provides an environment in which a user 1, a test taker, who wants to be provided the art psychological analysis service interacts with the meta information extraction device 10. In addition, the user interface 11 is a concept including a hardware device and a software program to receive an instruction from the user 1 and convert the instruction into electronic data. For example, an input device such as a keyboard, a mouse, and a touch pen, an output device such as a display, and a drawing application which processes data, such as contours and colors, input through the input device to display the data on the output device in real time may be included.

That is, the meta information extraction device 10 allows the user interface 11 to interact with the user 1 so that the picture data 100 may be input from the user 1 through the meta information extraction device 10.

At this time, the picture data 100 is data which is generated on a screen of the meta information extraction device 10, and is configured by a combination of objects generated in a position designated by the user 1 after being selected from the library 14 by means of the user interface 10, by the user 1.

Further, the object selected by the user 1 may be information including an item which may become an evaluation element of an art psychological analysis (or an art psychological test).

Here, the art psychological test may be an HTP test which asks to draw at least one of a house, a tree, and a people which is an object and then analyzes a psychological state of the user from information such as a shape, a color, and a position of the picture. However, the method is not limited so as to analyze the personality of the user 1 by means of picture data 100 which is formed of combination of various objects. If the object is a house, items constituting the object may include house frames (a roof, a wall, and a chimney), windows, and doors, and if the object is a tree, stems, roots, leaves, and fruits may be included.

The first feature extraction unit 12 is trained by the artificial intelligence model to extract objects from picture data 100 which is generated with a combination of objects by the user 1. The artificial intelligence model refers to a learning model configured by a plurality of layers to implement a function similar to a human neural network, and an artificial neural network model such as a recurrent neural network (RNN), a convolutional neural network (CNN), and an attention based model may be used.

An example of a process of training the first feature extraction unit 12 by means of the artificial intelligence model is as follows.

Figure 2:
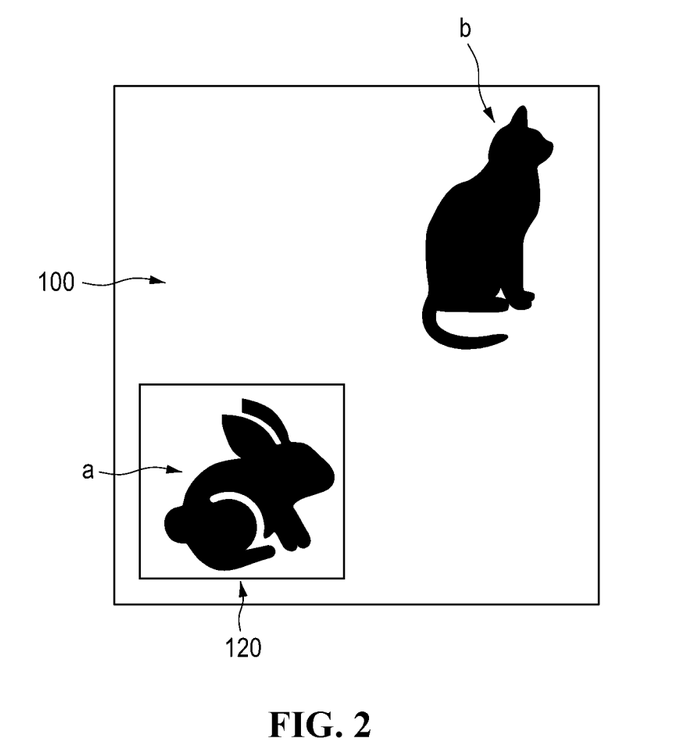
FIG. 2 is a view illustrating an example of picture data including an object extracted by a first feature extraction unit according to the present disclosure.

FIG. 2 is a view illustrating an example of picture data including an object extracted by a first feature extraction unit according to the present disclosure.

Referring to FIG. 2, the user 1 generates picture data 100 with a combination of objects whose meta information is stored in a library 14, and the picture data 100 may include a first object a, a "rabbit", and a second object b, a "cat", whose meta information is stored in the library 14.

In the picture data 100, various objects (for example, animals, insects, buildings, and transportations) may be included by the user 1, as well as the first and second objects a and b.

Hereinafter, the first feature extraction unit 12 and the second feature extraction unit 13 will be described in detail with respect to the first object a.

The first feature extracting unit 12 extracts a first object a from the picture data 100. In order to extract the first object a, an area enclosing the first object a is set in the picture data 100 to extract detailed picture information 120 with the area as a background, and the first object a may be extracted from the detailed picture information 120.

Further, the first feature extraction unit 12 transforms or adjusts a size value, an angle value, and a position value of the first object a extracted from the detailed picture information 120 to a size value, an angle value, and a position value which is applicable to the picture data 100 to extract a plurality of first objects a's having different size values, angle values, and position values from one first object a.

At this time, the size value, the angle value, and the position value of the first object a which is transformed or adjusted by the first feature extraction unit 12 are not limited, but for the better understanding of the present disclosure, an example of the size value, the angle value, and the position value of the first object a obtained by transforming or adjusting the first object a extracted from the detailed picture information 120 is as follows.

The first object a with a transformed or adjusted size value from the first object a extracted from the detailed picture information 120 may be an object with a magnification to the first object a extracted from the detailed picture information 120 which is at least one of 1:2, 1:5, and 1:10, and a length (width) which is reduced or transformed by 2 to 10 times as compared with the first object a extracted from the detailed picture information 120.

The first object a with a transformed or adjusted angle value from the first object a extracted from the detailed picture information 120 may be an object which rotates at least one angle of 1 to 359° from the first object a extracted from the detailed picture information 120.

The first object a with a transformed or adjusted position value from the first object a extracted from the detailed picture information 120 is a coordinate on which the first object a is possibly disposed on the picture data 100, excluding a coordinate of the first object a extracted from the detailed picture information 120.

The second feature extraction unit 13 is trained with the artificial intelligence model to extract meta information 130 about a plurality of first objects a's extracted by the first feature extraction unit 12. The artificial intelligence model refers to a learning model configured by a plurality of layers to implement a function similar to a human neural network, and an artificial neural network model such as a recurrent neural network (RNN), a convolutional neural network (CNN), and an attention based model may be used.

Figure 3:
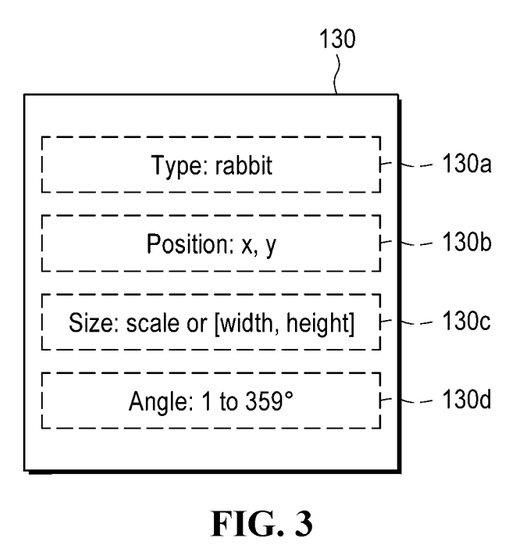
FIG. 3 is a view illustrating an example of meta information of an object extracted by a second feature extraction unit according to the present disclosure.

FIG. 3 is a view illustrating an example of meta information of an object extracted by a second feature extraction unit according to the present disclosure.

Referring to FIG. 3, the second feature extraction unit 13 is trained by the artificial intelligence model to extract meta information 130 of the first object a including at least a type 130a, a position value 130b, a size value 130c, and an angle value 130d of the first object a, respectively, from a plurality of first objects a.

At this time, the type 130a of the first object a extracted from the second feature extraction unit 13 may be "rabbit", and the remaining position value 130b, size value 130c, and angle value 130d of the first object a are not limited, but the position value 130b, the size value 130c, and the angle value 130d may be extracted by the second feature extraction unit 13 as follows.

Figure 4:
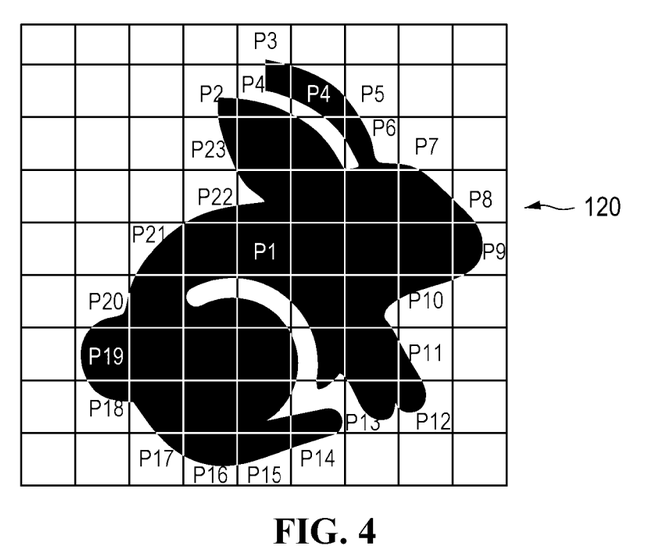
FIG. 4 is a view illustrating an example of detailed picture information for explaining a method of extracting a position and a size value of an object which is meta information by a second feature extraction unit according to the present disclosure.

FIG. 4 is a view illustrating an example of detailed picture information for explaining a method of extracting a position and a size value of an object which is meta information by a second feature extraction unit according to the present disclosure.

Referring to FIG. 4, the second feature extraction unit 13 may extract a coordinate (x, y) of a center pixel P1, among pixels which configure the first object a generated by pre-processing detailed picture information 120 including the first object a from which meta information 130 of the first object a is extracted, in the pixel units, as the position value 130b of the first object a.

Further, the second feature extraction unit 13 may extract, by comparing with the first object a of the detailed picture information 120, a magnification of reducing and enlarging the first object a from which the meta information 130 is extracted, and the size value 130c including a width value and a length value of the first object a.

The width and length values of the first object a may be calculated by a value of each pixel coordinate (x, y) which forms sets P2 to P23 of outer pixels enclosing the first object a, among pixels which configure the first object a generated by preprocessing detailed picture information 120 including the first object a from which the meta information 130 is extracted by the second feature extraction unit 13 in the pixel units.

Moreover, a width value of the first object a, between the width and length values of the first object a refers to a left and right (horizontal) length of the first object a so that the width value may be calculated by an x-coordinate value of each pixel which forms sets P2 to P23 of the outer pixel, and the length value of the first object a refers to an up and down (vertical) length of the first object a so that the length value may be calculated by the y coordinate value of each pixel which forms the sets P2 to P23 of the outer pixel.

In the meantime, the second feature extraction unit 13 compares the detailed picture information 120 and the meta information 130 to extract the angle value 130d of the first object a by a rotating degree of the first object a from which the meta information 130 is extracted, based on the angle value of the first object a extracted from the detailed picture information 120.

The library 14 stores an object extracted from the detailed picture information 120 by the first feature extraction unit 12, and meta information 130 about a plurality of objects extracted from the second feature extraction unit 13.

The meta information extraction device 10 stores the object in the library 14 so that when the user 1 generates the picture data 100, the object a of which information is stored in the library 14 is included on the picture data 100.

As described above, the user 1 does not directly draw the object (picture), but the picture data 100 is generated by a combination of objects whose information is stored in the library 14. Accordingly, the user 1 may generate the picture data by the combination of the object in a short time. Further, in the expression of the object which may become a subjective problem because every user have different expression ways for the object, the dimension and the range of the problem are limited like multiple choice problems, to narrow the range of the psychological state of the user to be analyzed (interpreted) through the art psychological analysis system and method to be described.

Further, the meta information extraction device 10 generates the picture data 100 with an object a whose information is stored in the library 14 so that user 1 who lacks a drawing skill to express the subject may easily take the art psychological test.

The meta information extraction device 10 stores the meta information 130 of the object in the library 14 to construct the artificial intelligence model using meta information 130 of the object, rather than the pixel units. When objects from which the meta information 130 is extracted are disposed on the picture data 100 with different sizes and directions, where the object is located is labeled to train the artificial intelligence model only with the meta information 130 of the object.

Hereinafter, an art psychological analysis system which may analyze a psychological state of a test taker using the meta information extraction device 10 will be described in detail.

Figure 5:
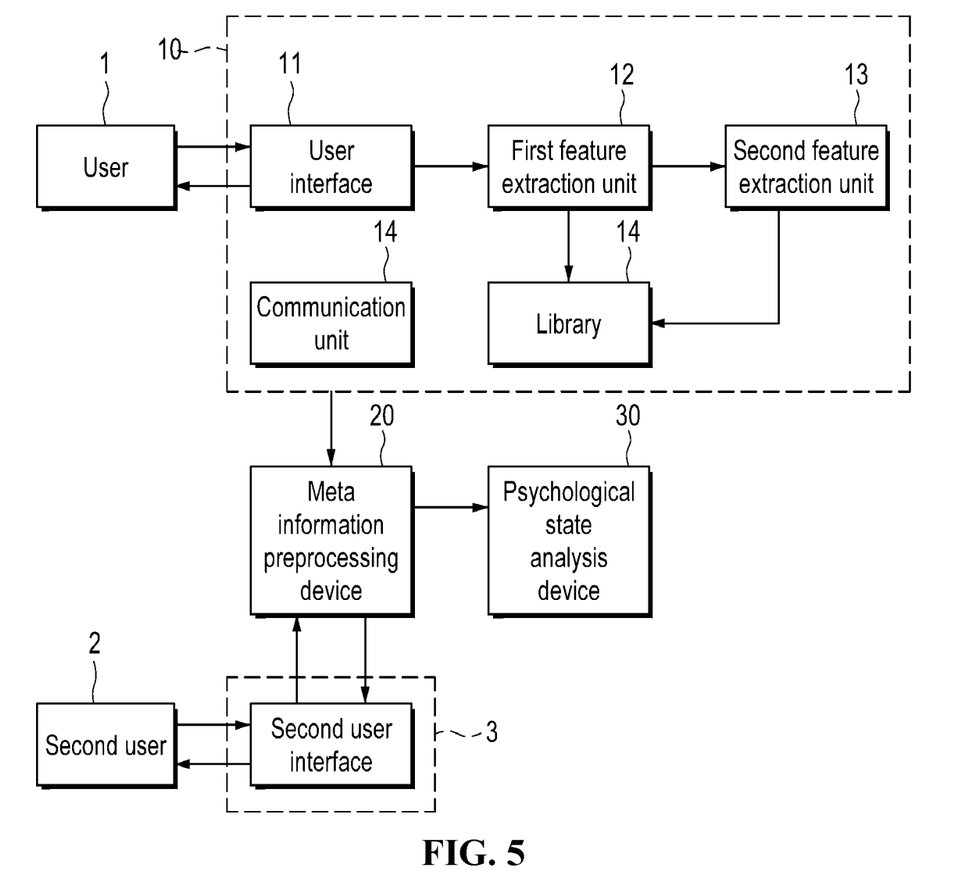
FIG. 5 is a block diagram illustrating an art psychological analysis system using a meta information extraction device of an object for an artificial intelligence art psychological test according to the present disclosure.

FIG. 5 is a block diagram illustrating an art psychological analysis system using a meta information extraction device of an object for an artificial intelligence art psychological test according to the present disclosure.

Referring to FIG. 5, the art psychological analysis system according to the exemplary embodiment of the present disclosure includes the meta information extraction device 10, a meta information preprocessing device 20, and a psychological analysis device 30.

The meta information preprocessing device 20 adds, to the meta information 130 of the object stored in the library 14, a psychological analysis opinion about the meta information 130 of the object received from the second user's terminal 3 carried by the second user 2 who is a tester (a picture analysis expert).

At this time, it is desirable that the meta information preprocessing device 20 receives the meta information 130 of the object from the library 14 to allow the second user 2 to receive the meta information 130 of the object, and adds the psychological analysis opinion received from the terminal 3 of the second user to the meta information 130 of the object.

Further, the terminal 3 of the second user receives the meta information 130 of the object from the meta information preprocessing device 20 to provide to the second user 2, and the terminal 3 of the second user may include a second user interface to allow the second user 2 to input the psychological analysis opinion about the provided meta information 130.

The terminal 3 of the second user transmits the psychological analysis opinion about the meta information 130 input from the second user 2 to the meta information preprocessing device 20. The meta information preprocessing device 20 adds the psychological analysis opinion of the user 1 to the meta information 130 of the object, which is transmitted to the psychological state analysis device 30.

The psychological state analysis device 30 is trained by the artificial intelligence model to analyze the psychological state of the user 1 by the combination of the meta information 130 of the object to which the psychological analysis opinion is added by the meta information preprocessing device 20. In addition, information about the analyzed psychological state of the user 1 is transmitted to the meta information extraction device 10.

The repeated contents to the detailed description with reference to FIGS. 1 to 4 will be omitted for the sake of convenience, and the meta information extraction device 10 includes a communication unit 15 for receiving information about the psychological state of the user 1 from the psychological state analysis device 30.

When the meta information extraction device 10 receives the information about the psychological state of the user 1 by means of the communication unit 15, the meta information extraction device 10 removes (erases) the picture data 100 generated by the user 1 and then displays the information about the psychological state of the user on the screen.

Moreover, after loading (refreshing) the picture data 100, the meta information extraction device 10 may display information about the psychological state of the user 1 on the screen together with the picture data 100.

The communication unit 15 not only receives the information about the psychological state of the user 1, but also transmits the meta information 130 of the object to the meta information preprocessing device 20 to cause the meta information preprocessing device 20 to preprocess the meta information 130 of the object stored in the library 14.

Hereinafter, processes of an art psychological analysis method which may analyze a psychological state of a test taker using the meta information extraction apparatus 10 will be described in detail.

Figure 6:
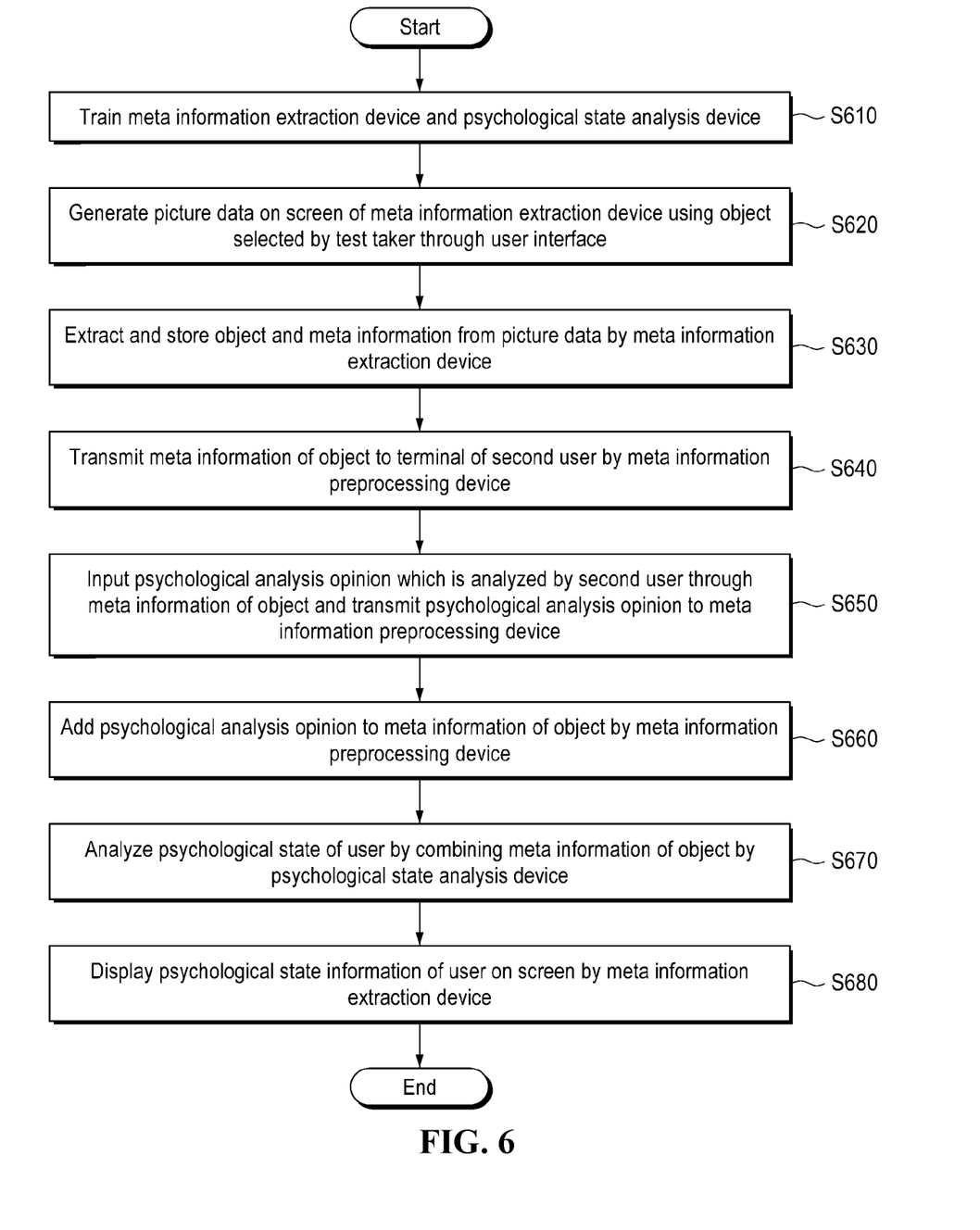
FIG. 6 is a flowchart illustrating processes of an art psychological analysis method using a meta information extraction device of an object for an artificial intelligence art psychological test according to the present disclosure.

FIG. 6 is a flowchart illustrating processes of an art psychological analysis method using a meta information extraction device of an object for an artificial intelligence art psychological test according to the present disclosure.

Referring to FIG. 6, the meta information extraction device 10 and the psychological state analysis device 30 may be trained in step S610.

Next, the user 2 who is a test taker may generate picture data 100 on a screen of the meta information extraction device 10 by a combination of objects which are loaded to be selected from the library 14 through the user interface 10 in step S620.

Next, the meta information extraction device 10 extracts object from the picture data 100 and meta information 130 from the object by the first and second feature extraction units 12 and 13, and then may store the object and the meta information 130 in the library 14 in step S630.

Next, the meta information preprocessing device 20 receives the meta information 130 of the object from the library 14 through the communication unit 15, and may transmit the meta information 130 of the object to the terminal 3 of the second user carried by the second user 2 who is a tester in step S640.

Next, the second user 2 inputs a psychological analysis opinion obtained by analyzing the meta information 130 of the object to the terminal 3 of the second user, and the terminal 3 of the second user may transmit the psychological analysis opinion input by the second user 2 to the meta information preprocessing device 20 in step S650.

Next, the meta information preprocessing device 20 adds the psychological analysis opinion received from the terminal 3 of the second user to the meta information 130 of the object received from the library 14 to preprocess the meta information 130 of the object in step S660.

Next, the psychological state analysis device 30 combines the meta information 130 of the object to which the psychological analysis opinion of the user 1 is added to analyze the psychological state of the user 1 in step S670.

Next, the meta information extraction device 10 receives information about the psychological state of the user 1 analyzed by the psychological state analysis device 30, and, when the information about the psychological state of the user 1 is received, removes the picture data 100 and then may display information about the psychological state of the user 1 on the screen in step S680.

At this time, in step S680, after loading (refreshing) the picture data 100, the meta information extraction device 10 may display information about the psychological state of the user 1 on the screen together with the picture data 100.

In the meantime, the art psychological analysis method according to the present disclosure may be implemented by an application or implemented in the form of a program command which may be executed through various computer components to be recorded in a computer readable recording medium. The computer readable recording medium may include solely a program command, a data file, and a data structure or a combination thereof.

Examples of the computer readable recording medium include magnetic media such as a hard disk, a floppy disk, or a magnetic tape, optical recording media such as a CD-ROM or a DVD, magneto-optical media such as a floptical disk, and a hardware device which is specifically configured to store and execute the program command such as a ROM, a RAM, and a flash memory.

As described above, the detailed description of the exemplary embodiments of the disclosed present disclosure is provided such that those skilled in the art implement and carry out the present disclosure. While the disclosure has been described with reference to the preferred embodiments, it will be understood by those skilled in the art that various changes and modifications of the present disclosure may be made without departing from the spirit and scope of the disclosure. For example, those skilled in the art may use configurations disclosed in the above-described exemplary embodiments by combining them with each other. Therefore, the present disclosure is not intended to be limited to the above-described exemplary embodiments but to assign the widest scope consistent with disclosed principles and novel features.

The present disclosure may be implemented in another specific form within the scope without departing from the technical spirit and essential feature of the present disclosure. Therefore, the detailed description should not restrictively be analyzed in all aspects and should be exemplarily considered. The scope of the present disclosure should be determined by rational interpretation of the appended claims and all changes are included in the scope of the present disclosure within the equivalent scope of the present disclosure. The present disclosure is not intended to be limited to the above-described exemplary embodiments but to assign the widest scope consistent with disclosed principles and novel features. Further, claims having no clear quoting relation in the claims are combined to configure the embodiment or may be included as new claims by correction after application.

The invention claimed is:

1. An art psychological analysis system for an artificial intelligence art psychological test, the system comprising:
   a meta information extraction device including:
   a user interface for providing an interactive environment to a first user who is a test taker;
   a first feature extraction unit which is trained by an artificial intelligence model to extract an object from picture data generated on a screen using the object selected by the first user through the user interface,
   wherein the picture data is configured by a combination of a plurality of objects generated in a position designated by the first user after being selected from a library through the user interface by the first user, and
   wherein the first feature extraction unit extracts detailed picture information with an area set in the picture data as a background, and extracts the object from the detailed picture information; and
   a second feature extraction unit which is trained by the artificial intelligence model to extract meta information of the object extracted by the first feature extraction unit,
   wherein the second feature extraction unit extracts each meta information of the object including at least a type, a size value, an angle value, and a position value of the object from the plurality of objects, and
   wherein the library which stores the object extracted by the first feature extraction unit and the meta information extracted by the second feature extraction unit;
   a meta information preprocessing device which receives the meta information from the meta information extraction device and a psychological analysis opinion obtained by analyzing the meta information input from a terminal of a second user who is a tester, and adds the psychological analysis opinion to the meta information; and
   a psychological state analysis device which is trained by the artificial intelligence model to analyze a psychological state of the first user with a combination of the meta information to which the psychological analysis opinion received from the meta information preprocessing device is added.

2. The art psychological analysis system of claim 1, wherein the first feature extraction unit transforms or adjusts a size value, an angle value, and a position value of the object extracted from the detailed picture information to a size value, an angle value, and a position value which are applicable to the picture data to extract the plurality of objects from the object.

3. The art psychological analysis system of claim 1, wherein the position value of the object is a coordinate of a center pixel, among pixels which configure the object generated by preprocessing detailed picture information including the object from which the meta information is to be extracted by the second feature extraction unit in pixel units.

4. The psychological analysis system of claim 1, wherein the size value of the object includes, based on the object extracted from the detailed picture information, a magnification of reducing or enlarging the object from which the meta information is to be extracted, and width and length values of the object.

5. The art psychological analysis system of claim 4, wherein the width and length values of the object are calculated by x and y coordinate values of each pixel which forms sets of outer pixels enclosing the object, among pixels which configure the object which is generated by preprocessing the detailed picture information including the object from which the meta information is to be extracted by the second feature extraction unit, in pixel units.

6. The psychological analysis system of claim 1 wherein the angle value of the object is a rotating degree of the object from which the meta information is to be extracted, based on an angle value of the object extracted from the detailed picture information.

7. An art psychological analysis system for an artificial intelligence art psychological test, the system comprising:
   a meta information extraction device which is trained by an artificial intelligence model to extract an object from picture data generated on a screen by selecting the object by a first user who is a test taker and meta information from the object, and stores the extracted object and the meta information,
   wherein the meta information extraction device includes:
   a user interface for providing an interactive environment to the first user who is the test taker;
   a first feature extraction unit which is trained by the artificial intelligence model to extract the object from the picture data generated on the screen using the object selected by the first user through the user interface,
   wherein the picture data is configured by a combination of a plurality of objects generated in a position designated by the first user after being selected from a library through the user interface by the first user, and
   wherein the first feature extraction unit extracts detailed picture information with an area set in the picture data as a background, and extracts the object from the detailed picture information; and
   a second feature extraction unit which is trained by the artificial intelligence model to extract the meta information of the object extracted by the first feature extraction unit,
   wherein the second feature extraction unit extracts each meta information of the object including at least a type, a size value, an angle value, and a position value of the object from the plurality of objects, and
   wherein the library which stores the object extracted by the first feature extraction unit and the meta information extracted by the second feature extraction unit;
   a meta information preprocessing device which receives the meta information from the meta information extraction device and a psychological analysis opinion obtained by analyzing the meta information input from a terminal of a second user who is a tester, and adds the psychological analysis opinion to the meta information; and a psychological state analysis device which is trained by the artificial intelligence model to analyze a psychological state of the first user with a combination of the meta information to which the psychological analysis opinion received from the meta information preprocessing device is added.

8. The art psychological analysis system of claim 7, wherein the meta information extraction device receives information about the psychological state of the first user from the psychological state analysis device, and displays information about the psychological state of the first user on the screen of the meta information extraction device after removing the picture data.

9. An art psychological analysis method for an artificial intelligence art psychological test, the method comprising:

training a meta information extraction device and a psychological state analysis device;

generating picture data on a screen of the meta information extraction device using an object selected by a first user who is a test taker through a user interface;

applying a first extraction unit which is trained by an artificial intelligence model to extract the object from the picture data generated on the screen using the object selected by the first user through the user interface, wherein the picture data is configured by a combination of a plurality of objects generated in a position designated by the first user after being selected from a library through the user interface by the first user, and wherein a first feature extraction unit extracts detailed picture information with an area set in the picture data as a background, and extracts the object from the detailed picture information; and applying a second feature extraction unit which is trained by the artificial intelligence model to extract meta information of the object extracted by the first feature extraction unit, wherein the second feature extraction unit extracts each meta information of the object including at least a type, a size value, an angle value, and a position value of the object from the plurality of objects;

storing the object and meta information in the library, by the meta information extraction device, after extracting the object from the picture data and the meta information from the object;

transmitting the meta information, by a meta information preprocessing device, to a terminal of a second user who is a tester, after receiving the meta information from the meta information extraction device;

allowing the second user to input a psychological analysis opinion obtained by analyzing meta information through a terminal of the second user and transmit the psychological analysis opinion to the meta information preprocessing device;

adding the psychological analysis opinion received from the terminal of the second user to meta information, by the meta information preprocessing device;

and analyzing a psychological state of the first user with a combination of the meta information to which the psychological analysis opinion received from the meta information preprocessing device, by the psychological state analysis device.

10. The art psychological analysis method using a meta information extraction device of an object for an artificial intelligence art psychological test of claim 9, the method further comprising: receiving information about the psychological state of the first user, by the meta information extraction device, from the psychological state analysis device, and displaying information about the psychological state of the first user on the screen of the meta information extraction device after removing the picture data.

11. A non-transitory computer readable storage medium storing executable instructions, wherein the instructions, when executed by a processor, cause the processor to perform the art psychological analysis method of claim 10.

12. A non-transitory computer readable storage medium storing executable instructions, wherein the instructions, when executed by a processor, cause the processor to perform the art psychological analysis method of claim 9.

* * * * *